ða (12) United States Patent
Bates et al.

(10) Patent No.: US 8,911,710 B2
(45) Date of Patent: Dec. 16, 2014

(54) INTRAVASCULAR CONTRAST AGENTS

(75) Inventors: Roderick Wayland Bates, Singapore (SG); Xavier Golay, London (GB); Changtong Yang, Singapore (SG)

(73) Assignees: Agency for Science, Technology and Research, Connexis (SG); Nanyang Technological University, Singapore (SG)

( * ) Notice: Subject to any disclaimer, the term of this patent is extended or adjusted under 35 U.S.C. 154(b) by 532 days.

(21) Appl. No.: 13/103,369

(22) Filed: May 9, 2011

(65) Prior Publication Data

US 2011/0268663 A1  Nov. 3, 2011

Related U.S. Application Data

(63) Continuation of application No. PCT/SG2009/000418, filed on Nov. 11, 2009.

(60) Provisional application No. 61/113,277, filed on Nov. 11, 2008.

(51) Int. Cl.
| | |
|---|---|
| *A61B 5/055* | (2006.01) |
| *C07D 225/00* | (2006.01) |
| *A61B 5/05* | (2006.01) |
| *C07D 257/02* | (2006.01) |
| *A61K 49/08* | (2006.01) |
| *A61K 49/14* | (2006.01) |
| *C07F 5/00* | (2006.01) |

(52) U.S. Cl.
CPC ............ *C07D 257/02* (2013.01); *A61K 49/085* (2013.01); *A61K 49/146* (2013.01); *C07F 5/003* (2013.01)
USPC ................. 424/9.363; 424/9.364; 424/9.365; 540/465; 600/410

(58) Field of Classification Search
CPC .............. A61K 49/106; A61K 49/108; A61K 47/48246; A61K 49/085; A61K 49/146; C07F 5/003; C07D 257/02
USPC ................. 424/9.364, 9.365, 9.363; 540/465; 600/410
See application file for complete search history.

(56) References Cited

U.S. PATENT DOCUMENTS

| | | | | |
|---|---|---|---|---|
| 4,885,363 | A | * | 12/1989 | Tweedle et al. ............... 540/465 |
| 2004/0146463 | A1 | | 7/2004 | Meade et al. |
| 2006/0233704 | A1 | * | 10/2006 | Maecke et al. ............... 424/1.49 |

FOREIGN PATENT DOCUMENTS

| | | | |
|---|---|---|---|
| WO | WO 2005/001415 | A2 | 1/2005 |
| WO | WO 2008/073458 | A2 | 6/2008 |

OTHER PUBLICATIONS

Hainsworth et al., Bioconjugate Chem., 2005, 16,p. 1468-1474.*

(Continued)

*Primary Examiner* — Michael G Hartley
*Assistant Examiner* — Leah Schlientz
(74) *Attorney, Agent, or Firm* — Woodard, Emhardt, Moriarty, McNett & Henry LLP

(57) ABSTRACT

Intravascular contrast agents are provided by Gd-chelates modified so as to comprise an amino acid unit attached to the chelate via a linker group suitably selected from $C_{2-4}$alkylene and $C_{3-5}$alkynylene. The chelates may be used as an intravascular contrast agent for MRI. Certain embodiments demonstrate enhanced relaxivity and good levels of signal enhancement.

14 Claims, 1 Drawing Sheet

(56) References Cited

OTHER PUBLICATIONS

Figure 1:
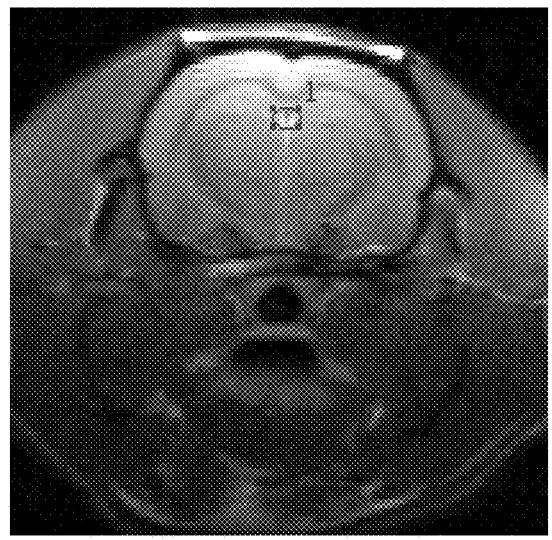

Allen et al. "Tryptophan and tyrosine to terbium fluoresence resonance energy transfer as a method to "map" aromic residues and monitor docking", Biochemical and Biophysical Research Communications 349 (2006), pp. 1264-1268

Caravan, Peter, "Strategies for increasing the sensitivity of gadolinium based MRI contrast agents", Chem. Soc. Rev., 2006, 35, pp. 512-523.

Crich et al., "In Vitro and in Vivo Magnetic Resonance Detection of Tumor Cells by Targeting Glutamine Transporters with Gd-Based Probes", J. Med. Chem. 2006, 49, pp. 4926-4936.

Lattuada et al., "Magnetic resonance imaging of tumor cells by targeting the amino acid transport system", Bioorganic & Medicinal Chemistry Letters 16 (2006), pp. 4111-4114.

Yang et al., "Development of Novel Intravascular MRI Contrast Agents Using Gadolinium Chelates", Proc. Intl. Soc. Mag. Reson. Med. 17 (2009) p. 3126.

\* cited by examiner

INTRAVASCULAR CONTRAST AGENTS

FIELD OF THE INVENTION

The present invention is concerned with compounds that are suitable for use as contrast agents for magnetic resonance imaging (MRI) and in particular for contrast agents comprising Gadolinium chelates.

BACKGROUND

MRI has become one of the most important and prominent techniques in diagnostic clinical medicine. The most commonly used contrast agents (CAs) nowadays are thermodynamically and kinetically stable low molecular weight gadolinium complexes. However, current clinically available Gd-based contrast agents can be non-specific and inefficient. Indeed, current clinically available Gd-based contrast agents may suffer from drawbacks including rapid excretion and transient tissue retention.

Whilst macromolecular Gd complexes have been developed as intravascular CAs for blood pool and tumor angiogenesis because they may provide increased and prolonged contrast enhancement within the blood pool at low doses, large polymeric Gd complexes are associated with limitations, such as poorly defined architectures, unpredictable pharmacokinetics, and an increased possibility of Gd leakage from the Gd complex due to prolonged tissue retention.

SUMMARY OF THE INVENTION

One aspect of the present invention seeks to provide alternative and/or improved contrast agents as compared to known contrast agents. Embodiments of the present invention suitably provide contrast agents that are specific in terms of their targeting of particular parts of a patient's body or specific tissues. Embodiments of the present invention preferably provide efficient contrast agents, for example contrast agents having one or more of excellent relaxivity, signal enhancement, low toxicity, appropriate excretion rate and appropriate tissue retention.

The present inventors have undertaken the development of a new class of amino acid-containing contrast agents whereby an amino acid functionality is incorporated into the molecule via a linker group to a metal chelate, suitably a Gd-chelate.

In embodiments, as discussed below, these amino acid-containing contrast agents exhibit excellent characteristics when tested in rat MRI studies.

The present inventors have, also undertaken the development of a new class of oligomer-based contrast agents by incorporating gadolinium complexes and in particular multiple-gadolinium complexes into peptides of controlled length and structure.

The present inventors have found that this allows synthesis of large libraries of Gd-peptides with different sequences, peptide length and number of Gd-chelates. Furthermore, screening of such contrast agents and in particular of libraries of such compounds will suitably enable selection of oligomers with the properties desired. In embodiments, such screening will identify novel, efficient and selective MRI contrast agents.

One aspect of the present invention proposes that (1) a paramagnetic metal chelate be provided with an amino acid unit via a linker group and that such a compound be used as an intravascular contrast agent for MRI; and that (2) a peptide, suitably a comparatively short peptide, e.g. having 2 to 20 amino acid units (referred to herein as an oligopeptide), can be provided with one, preferably at least two, paramagnetic metal chelates.

The present invention proposes that (1) by controlling one or more of the metal chelate, the linker and the amino acid unit, the contrast agent can be tailored, for example so that it becomes more specific for a particular location in the patient's body and/or exhibits better relaxitivity and/or signal enhancement, and that (2) by controlling one or both of the composition of the (oligo)peptide and the number of paramagnetic metal chelates, the contrast agent can be tailored so that it becomes more specific for a particular location in the patient's body and/or exhibits better relaxity and/or signal enhancement.

It is to be noted that in the case where a contrast agent of the present invention comprises a linker group, the linker group can be any suitable linker group, which groups the skilled reader would be able to identify from their common general knowledge in the light of the teaching of the present invention. In particular, the linker group suitably provides attachment of the amino acid unit or peptide to the metal chelate without interfering with the chelation of the metal of the metal chelate. Thus, the specific types of linker group set out in the claims are preferred examples only.

In a first aspect, the present invention provides a compound according to the following formula and pharmaceutically acceptable salts, hydrates, and solvates thereof

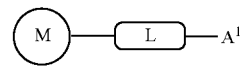

wherein

is a paramagnetic metal chelate,

is a linker group selected independently from $C_{1-6}$alkylene and $C_{2-6}$alkynylene and is optionally substituted, and $A^1$ is an amino acid or amino acid derivative.

In a further aspect, the present invention provides a compound according to the following formula and pharmaceutically acceptable salts, hydrates, and solvates thereof

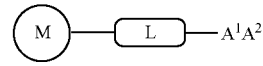

wherein

is a paramagnetic metal chelate,

is a linker group selected independently from $C_{1-6}$alkylene and $C_{2-6}$alkynylene and is optionally substituted, and each of $A^1$ and $A^2$ is selected independently from an amino acid and an amino acid derivative.

In a further aspect, the present invention provides a compound according to the following formula and pharmaceutically acceptable salts, hydrates, and solvates thereof

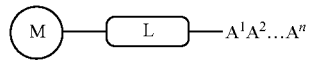

wherein

is a paramagnetic metal chelate,

is a linker group selected independently from $C_{1-6}$alkylene and $C_{2-6}$alkynylene and is optionally substituted, each of $A^1$ to $A^n$ is selected independently from an amino acid and an amino acid derivative, and n is in the range 2 to 20.

Preferably

is a Gd chelate.

Suitably the metal chelate comprises a nitrogen atom-containing ligand, suitably a ligand comprising at least 2 nitrogen atoms, preferably at least 3 nitrogen atoms and most preferably at least 4 nitrogen atoms.

Suitably the metal chelate comprises a nitrogen atom-containing macrocycle, preferably having at least 2, more preferably at least 3 and most preferably at least 4 nitrogen atoms (that is, the nitrogen atoms form part of the ligand/macrocycle such that they coordinate to the metal when the metal chelate comprises a metal.

In embodiments the metal chelate comprises a nitrogen atom-containing ligand and the metal chelate is coupled to the amino acid portion via a nitrogen atom of the ligand.

Suitably the metal chelate comprises DOTA. More preferably the metal chelate is a Gd-DOTA.

Preferably the linker group is selected from $C_{2-4}$alkylene and $C_{3-5}$alkynylene and is optionally substituted. Most preferably the linker group is selected from $C_{2-3}$alkylene and $C_4$alkynylene and is optionally substituted.

Preferred substituents are described below. An oxo-substituent (=O) is particularly preferred, especially when the linker is alkylene.

In embodiments, the linker group is unsubstituted, especially when the linker group is alkynylene.

In particularly preferred embodiments the linker group is selected from:

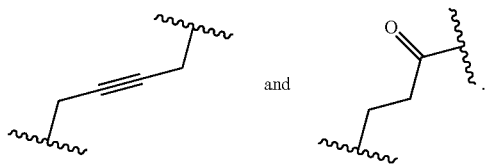 [SMILES: *CC#CC* ; *CCC(*)=O]

Preferably each of $A^1$ and $A^2$, if present, is selected independently from glutamic acid, a glutamic acid derivative, lysine and a lysine derivative. More preferably, each of $A^1$ and $A^2$, if present, is selected independently from a glutamic acid derivative and a lysine derivative.

Preferably $A^1$ is selected independently from:

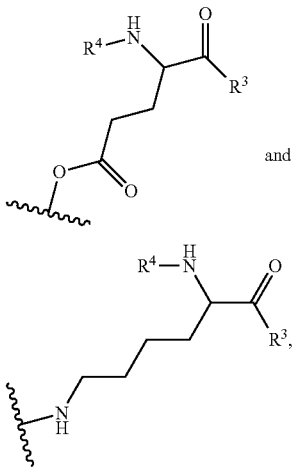

wherein $R^3$ is selected independently from $A^2$ as disclosed herein and —OMe, and $R^4$ is selected independently from $A^2$ as disclosed herein and —C(O)-Ph.

Preferably $A^1$ is selected independently from

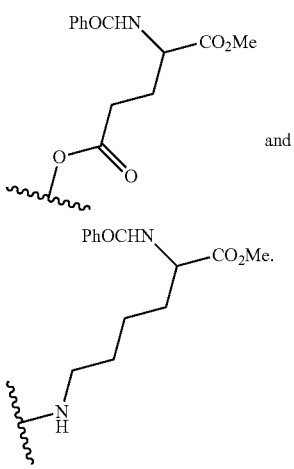

Preferably each of $A^1$ to $A^n$, if present, is selected independently from

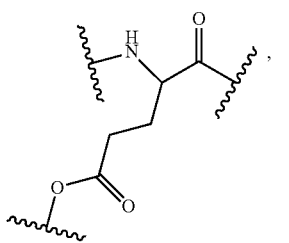

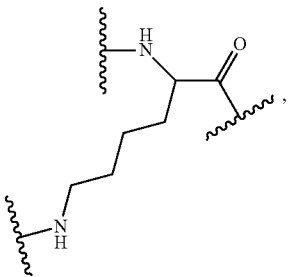

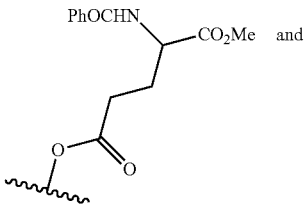

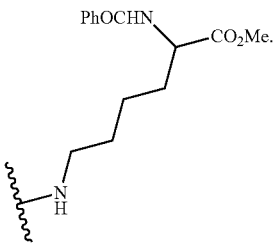

Preferably n, where present, is independently 2 to 10.

In a preferred embodiment and a further aspect, the present invention provides a compound selected from the following compounds and pharmaceutically acceptable salts, hydrates, and solvates thereof:

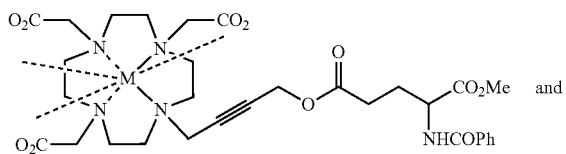

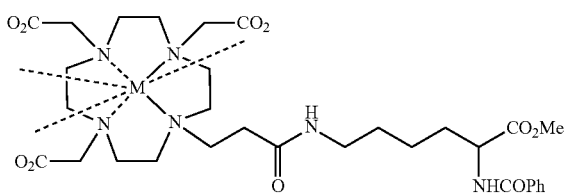

wherein M is a paramagnetic metal as described herein, preferably Gd.

Thus, particularly preferred compounds are as follows:

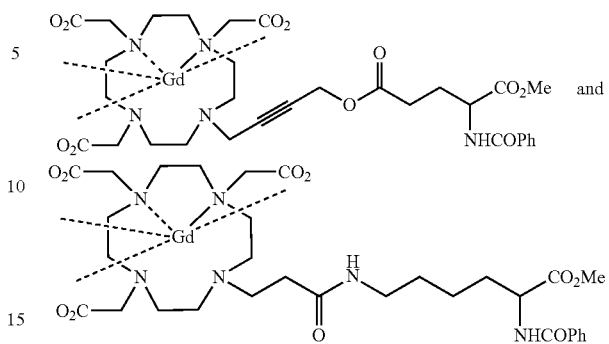

The compound may optionally include one or more water or other molecules (e.g. solvent molecules) coordinated to the metal.

In a particularly preferred embodiment, the compound is selected from compounds 1 and 2 pharmaceutically acceptable salts, hydrates, and solvates thereof:

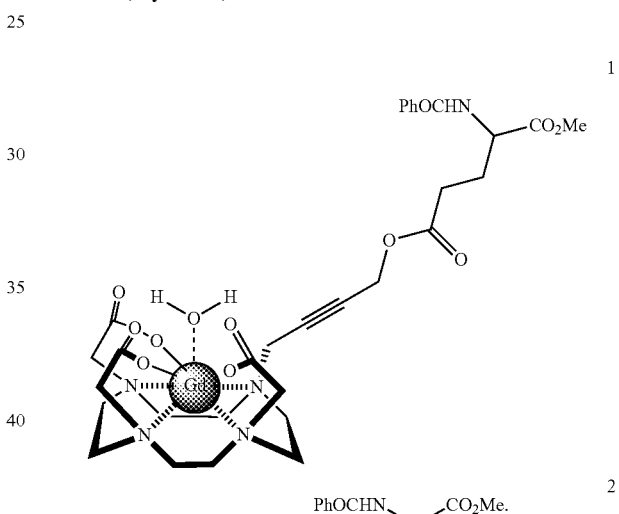

Whilst the above compounds are illustrated for convenience with a coordinating water molecule, the present invention also includes each compound in the absence of such a water molecule or more than one water molecule. Indeed, the present invention includes such compounds with other molecules, for example solvent molecules, coordinating to the Gd.

Furthermore, in a yet further aspect, the present invention provides a compound as defined herein in the absence of a metal. That is, the compound is a ligand to which a suitable metal, for example Gd, can be chelated. The structure of the ligand can be the same as that disclosed herein for the metal-containing (e.g. Gd-containing) compound.

Preferred compounds (ligands) are selected from the following compounds and pharmaceutically acceptable salts, hydrates, and solvates thereof:

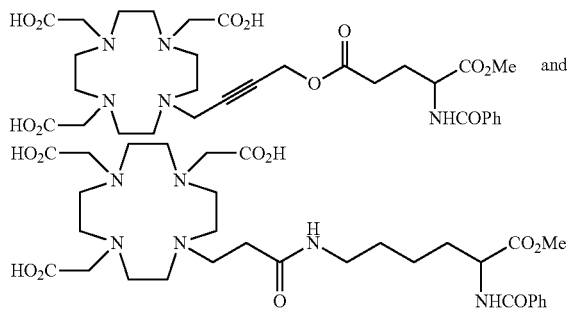

In a further aspect, the present invention provides a compound according to the previous aspects, which compound is a contrast agent for agent for magnetic resonance imaging (MRI), suitably an intravascular contrast agent.

In a further aspect, the present invention provides a contrast agent for magnetic resonance imaging (MRI) comprising a peptide and at least one paramagnetic metal chelate coupled to the peptide.

Preferably at least two paramagnetic metal chelates are coupled to the peptide.

Suitably the paramagnetic metal chelate is a Gd chelate. Preferably the paramagnetic metal chelate is Gd-DOTA.

Preferably the peptide comprises 2 to 20 amino acid units. Preferably the peptide comprises amino acid units selected from glutamic acid, a glutamic acid derivative, lysine and a lysine derivative.

Suitably the contrast agent comprises a paramagnetic metal chelate associated with at least 50% of the amino acid units of the peptide, preferably at least 75%, and most preferably at least 90%.

In a further aspect, the present invention provides a contrast agent for magnetic resonance imaging (MRI) comprising a paramagnetic metal chelate portion coupled to an amino acid portion, wherein the amino acid portion comprises at least two amino acid units.

Suitably the amino acid portion comprises an oligopeptide. Preferably the oligopeptide comprises 2 to 20 amino acid units. Preferably the oligopeptide comprises 2 to 10 amino acid units.

Suitably the paramagnetic metal chelate portion is a Gd chelate portion.

Preferably the contrast agent comprises at least two paramagnetic metal chelate portions coupled to the said amino acid portion.

Suitably at least 50% of the amino acid units in the amino acid portion have a paramagnetic metal chelate portion coupled thereto, preferably at least 75%, more preferably at least 90%, more preferably substantially all and most preferably a paramagnetic metal chelate portion is coupled to each of the amino acid units in the amino acid portion.

Suitably the contrast agent comprises 2 to 20 paramagnetic metal chelate portions coupled to the said amino acid portion.

Preferably the contrast agent comprises 2 to 10 paramagnetic metal chelate portions coupled to the said amino acid portion.

Suitably the or each amino acid unit in the amino acid portion is selected from glutamic acid, a glutamic acid derivative, lysine and a lysine derivative, more preferably the or each amino acid unit in the amino acid portion is selected from a glutamic acid derivative and a lysine derivative.

Preferably the or each amino acid unit in the amino acid portion is selected independently from

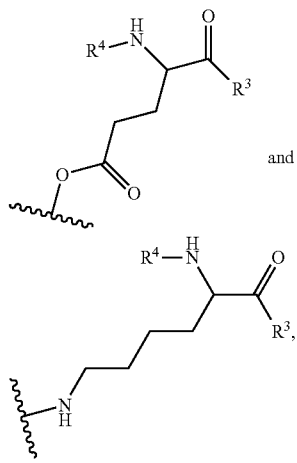

wherein $R^3$ is selected independently from an amino acid unit and —OMe, and $R^4$ is selected independently from an amino acid unit and —C(O)-Ph.

More preferably the or each amino acid unit in the amino acid portion is selected from:

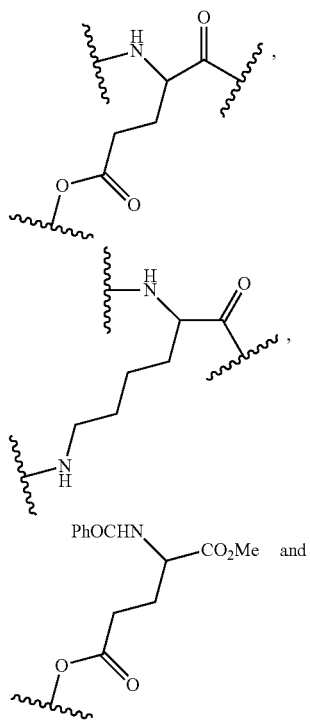

-continued

[Structure: PhOCHN-CH(CO2Me)-CH2CH2CH2CH2-NH-]

Preferably the chelate portion comprises a nitrogen atom-containing ligand, suitably a ligand comprising at least 2 nitrogen atoms, preferably at least 3 nitrogen atoms and most preferably at least 4 nitrogen atoms.

Suitably the chelate portion comprises a nitrogen atom-containing macrocycle. Preferably the chelate portion comprises DOTA.

Preferably the metal chelate portion is coupled to the amino acid portion via a linker group, the linker group being selected from $C_{1-6}$alkylene and $C_{2-6}$alkynylene and is optionally substituted. Suitably the linker group is selected from $C_{2-4}$alkylene and $C_{3-5}$alkynylene and is optionally substituted. Most preferably the linker group being selected from $C_{2-3}$alkylene and $C_4$alkynylene and is optionally substituted.

In particularly preferred embodiments the linker group is selected from

[Two linker structures shown: an alkyne-containing linker and a carbonyl-containing linker] and .

In embodiments the metal chelate portion comprises a nitrogen atom-containing ligand and the metal chelate portion is coupled to the amino acid portion via a nitrogen atom of the ligand.

In a further aspect, the present invention provides a contrast agent for magnetic resonance imaging (MRI) according to the following formula and pharmaceutically acceptable salts, hydrates, and solvates thereof $$[(M)-L-P]_n$$

wherein (M) is a paramagnetic metal chelate,

[L] is a linker group selected independently from $C_{1-6}$alkylene and $C_{2-6}$alkynylene and is optionally substituted,

[P] is a peptide wherein the number of amino acid units in the peptide is in the range 2 to 20, and n is independently 2 to 20.

In a further aspect, the present invention provides a contrast agent for magnetic resonance imaging (MRI) according to the following formula and pharmaceutically acceptable salts, hydrates, and solvates thereof $$R^5-[A^1]_n-R^6$$

wherein (M) is a paramagnetic metal chelate,

[L] is a linker group selected independently from $C_{1-6}$alkylene and $C_{2-6}$alkynylene and is optionally substituted, each of $R^5$ and $R^6$ is selected independently from H, —OMe, —C(O)-Ph,

[Structure with M-L-$A^1$]

and -$A^1$, each $A^1$ is selected independently from an amino acid and amino acid derivative, and n is independently 2 to 20.

In a further aspect, the present invention provides a contrast agent for magnetic resonance imaging (MRI) according to the following formula and pharmaceutically acceptable salts, hydrates, and solvates thereof.

$$R^5-[A]_n-R^6$$

wherein each A is selected independently from

[Structure with M-L-$A^1$]

and -[$A^1$]-, each of $R^5$ and $R^6$ is selected independently from H, —OMe, —C(O)-Ph,

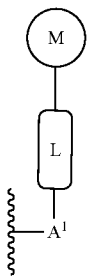

and -A¹,
wherein

is a paramagnetic metal chelate,

is a linker group selected independently from C₁₋₆alkylene and C₂₋₆alkynylene and is optionally substituted,
each A¹ is selected independently from an amino acid and amino acid derivative, and wherein:
n is independently 2 to 20.

Suitably the peptide comprises amino acids units independently as hereindefined.

Preferably

is a Gd chelate, more preferably a Gd-DOTA.
Preferably

is a linker group selected independently from C₂₋₄alkylene and C₃₋₅alkynylene and is optionally substituted. In embodiments,

is a linker group selected independently from

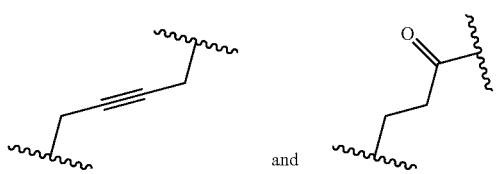

and

Preferably the peptide is selected independently from a linear peptide and a branched peptide.

Suitably the contrast agent is an intravascular contrast agent.

The present invention also includes the compounds in the absence of the Gd, i.e. the ligand. In a further aspect, the present invention provides a ligand for a contrast agent, wherein the ligand comprises the contrast agent as defined herein without the paramagnetic metal.

In a further aspect, the present invention provides a library comprising a plurality of contrast agents according to any one of the preceding claims.

Preferably each of the said plurality of contrast agents is different. Preferably each of the said plurality of contrast agents comprises a different amino acid portion or oligopeptide.

In a further aspect, the present invention provides a method of screening a library as defined herein.

Suitably the method is a method of screening to identify contrast agents that exhibit high relaxitivity and/or high signal enhancement.

A further aspect of the present invention provides a method of synthesising a contrast agent for magnetic resonance imaging (MRI), the method including the steps of (1) forming a monomeric amino acid metal chelate by attaching an amino acid unit to a paramagnetic metal chelate, and (2) forming an oligopeptide metal chelate by combining at least two monomeric amino acid metal chelates via their respective amino acid groups.

A further aspect of the present invention provides a method of modifying a paramagnetic metal chelate comprising a nitrogen atom-containing ligand, the method comprising the step of effecting conjugate addition of a nitrogen of the nitrogen atom-containing ligand to an acrylate ester.

Suitably the acrylate ester is selected so as to provide the metal chelate with a propionate group after conjugate addition.

Preferably the method includes the step of attaching an amino acid or peptide to the modified metal chelate.

In the case of a metal chelate that comprises a propionate group, suitably the amino acid or peptide is attached via the propionate group.

A further aspect of the present invention provides a method of synthesising a contrast agent as disclosed herein, the method including the step of synthesising a peptide and then coupling at least one paramagnetic metal chelate to the peptide.

Suitably the method includes coupling at least two paramagnetic metal chelates to the peptide.

A further aspect of the present invention provides a method of performing magnetic resonance imaging (MRI), wherein the contrast agent is a compound/contrast agent as disclosed herein. Preferably the method includes obtaining an image.

A further aspect of the present invention provides a method of administering a contrast agent to a patient, wherein the contrast agent is a compound/contrast agent as disclosed herein.

Suitably the step of administering the contrast agent includes injecting the patient.

A further aspect of the present invention provides a contrast agent for a diagnostic method practised on the human or animal body, wherein the contrast agent is a compound/contrast agent as disclosed herein.

A further aspect of the present invention provides a contrast agent for magnetic resonance imaging practised on the human or animal body, wherein the contrast agent is a compound/contrast agent as disclosed herein.

A further aspect of the present invention provides use of a compound/contrast agent as disclosed herein as a contrast agent, suitably as an intravascular contrast agent for MRI.

A further aspect of the present invention provides a compound having the structure of the contrast agent as defined herein.

A further aspect of the present invention provides a contrast agent composition comprising the compound of the previous aspect and a pharmaceutically acceptable carrier or diluent.

Contrast agents of the present invention comprising two or more amino acid units (e.g. 2 to 20 such units, i.e. a peptide) preferably have as their end or terminal groups, an amino acid unit, which amino acid unit can be optionally coupled to a paramagnetic metal chelate. Thus, the terminal amino acid unit can be with or without a metal chelate.

Any one of the aspects may be combined with any one or more of the other aspects. Furthermore, any one or more of the optional and preferred features of any one of the aspects may apply to any of the other aspects. In particular, features relating to a method or use may apply to a compound, contrast agent or composition, and vice versa.

DESCRIPTION OF PREFERRED EMBODIMENTS

The intravascular contrast agents of the present invention are described below with reference to certain preferred embodiments. The intravascular contrast agents of the present invention are also as set forth in applicants' International PCT Application No. PCT/SG2009/00418, filed Nov. 11, 2009, and applicants' U.S. Provisional Application No. 61/113,277, filed Nov. 11, 2008, the entire contents of which are hereby incorporated herein by reference. However, these embodiments are intended to assist in understanding the present invention, but not to restrict its scope. Various possible modifications and alterations to the form and the content of any particular embodiment could be conceived of by one skilled in the art without departing from the spirit and scope of the present invention, which is intended to be defined by the appended claims.

The term "paramagnetic metal" as used herein will be familiar to the skilled reader but for the avoidance of doubt it is intended to mean a metal that exhibits paramagnetism such that it is suitable for use as an MRI contrast agent. Gadolinium is the most preferred paramagnetic metal and any reference herein to a paramagnetic metal is also a reference to Gadolinium.

The term "amino acid unit" as used herein will be familiar to the skilled reader but for the avoidance of doubt it is intended to mean an amino acid, natural and non-natural, including in particular α-amino acids, or an amino acid derivative, wherein the amino acid or amino acid derivative is a mono-, bi- or tri-valent radical. In this connection the term "α-amino acid" as used herein pertains to compounds of the following formula:

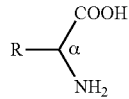

and the corresponding radicals, for example

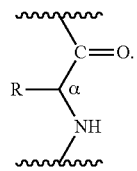

wherein the group R is an amino acid substituent, and can be, for example, a further amino acid.

Examples of α-amino acids include both natural amino acids and non-natural amino acids. The natural amino acids include: those with nonpolar (hydrophobic) R groups: alanine, Ala, A; isoleucine, Ile, I; leucine, Leu, L; methionine, Met, M; phenylalanine, Phe, F; proline, Pro, P; tryptophan, Trp, W; and valine, Val, V; those with polar but uncharged R groups: asparagine, Asn, N; cysteine, Cys, C; glutamine, Gln, Q; glycine, Gly, G; serine, Ser, S; threonine, Thr, T; and tyrosine, Tyr, Y; those with (potentially) positively charged R groups: arginine, Arg, R; histidine, His, H; and lysine, Lys, K; and those with (potentially) negatively charged R groups: aspartic acid, Asp, D; glutamic acid, Glu, E.

Examples of modified natural amino acids include, but are not limited to, hydroxyproline, γ-carboxyglutamate, and O-phosphoserine.

Examples of non-natural α-amino acids include: β-(napth-2-yl)alanine, β-(2-cyanophenyl) alanine, β-(ethinyl)alanine, β-(furan-2-yl)alanine, β-(thien-2-yl)alanine, and β-(4-pyridinyl)alanine.

As discussed herein, preferred amino acid units are glutamic acid and lysine, as well as derivatives thereof. Indeed, any reference herein to an amino acid unit is also a reference to one or more of glutamic acid, lysine, and derivatives thereof.

The term "amino acid derivatives" as used herein pertains to amino acid units that have been modified, for example to remove or substitute one or more atoms or functional groups. An example would be the substitution of a hydrogen for another monovalent atom or for a further group or compound. For example, the amino acid may be modified so that it comprises a biological ligand or lipophilic group as discussed herein, or one or more other amino acid units, for example joined via peptide bonds.

The term "peptide" as used herein will be familiar to the skilled reader but for the avoidance of doubt pertains to oligomeric or polymeric species formed from amino acid units, which units are linked together by an amide bond (also known as a peptide bond). As discussed herein a preferred number of amino acid units in a peptide is between 2 and 20, although a greater number of amino acid units is possible, for example up to 25, up to 30, up to 35 or even up to 40. Comparatively short chain peptides of this sort are also referred to herein as oligopeptides.

Certain Preferred Substituents

In one preferred embodiment, the substituent(s), often referred to herein as R, are independently selected from: oxo; halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., unsubstituted $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s), often referred to herein as R, are independently selected from:

—F, —Cl, —Br, and —I;
—OH;
=O;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;

—C(=O)OH;

—C(=O)OMe, —C(=O)OEt, and —C(=O)O(tBu);

—C(=O)NH$_2$, —C(=O)NHMe, —C(=O)NMe$_2$, and —C(=O)NHEt;

—NHC(=O)Me, —NHC(=O)Et, —NHC(=O)Ph, succinimidyl, and maleimidyl;

—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;

—CN;

—NO$_2$;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, and —CH$_2$CF$_3$;

—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;

—CH$_2$OH, —CH$_2$CH$_2$OH, and —CH(OH)CH$_2$OH;

—CH$_2$NH$_2$, —CH$_2$CH$_2$NH$_2$, and —CH$_2$CH$_2$NMe$_2$; and, optionally substituted phenyl.

In one preferred embodiment, the substituent(s), often referred to herein as R, are independently selected from: =O, —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

In one preferred embodiment, the substituent(s), often referred to herein as R, are independently selected from: =O; hydroxy; ether (e.g., C$_{1-7}$alkoxy); ester; amido; amino; and, C$_{1-7}$alkyl (including, e.g., unsubstituted C$_{1-7}$alkyl, C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl).

In one preferred embodiment, the substituent(s), often referred to herein as R, are independently selected from:

—OH;

=O;

—OMe, —OEt, —O(tBu), and —OCH$_2$Ph;

—C(=O)OMe, —C(=O)OEt, and —C(=O)O(tBu);

—C(=O)NH$_2$, —C(=O)NHMe, —C(=O)NMe$_2$, and —C(=O)NHEt;

—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;

-Me, -Et, -nPr, -iPr, -nBu, -tBu;

—CF$_3$, —CHF$_2$, —CH$_2$F, —CCl$_3$, —CBr$_3$, —CH$_2$CH$_2$F, —CH$_2$CHF$_2$, and —CH$_2$CF$_3$;

—CH$_2$OH, —CH$_2$CH$_2$OH, and —CH(OH)CH$_2$OH; and,

—CH$_2$NH$_2$, —CH$_2$CH$_2$NH$_2$, and —CH$_2$CH$_2$NMe$_2$.

Figure 2:
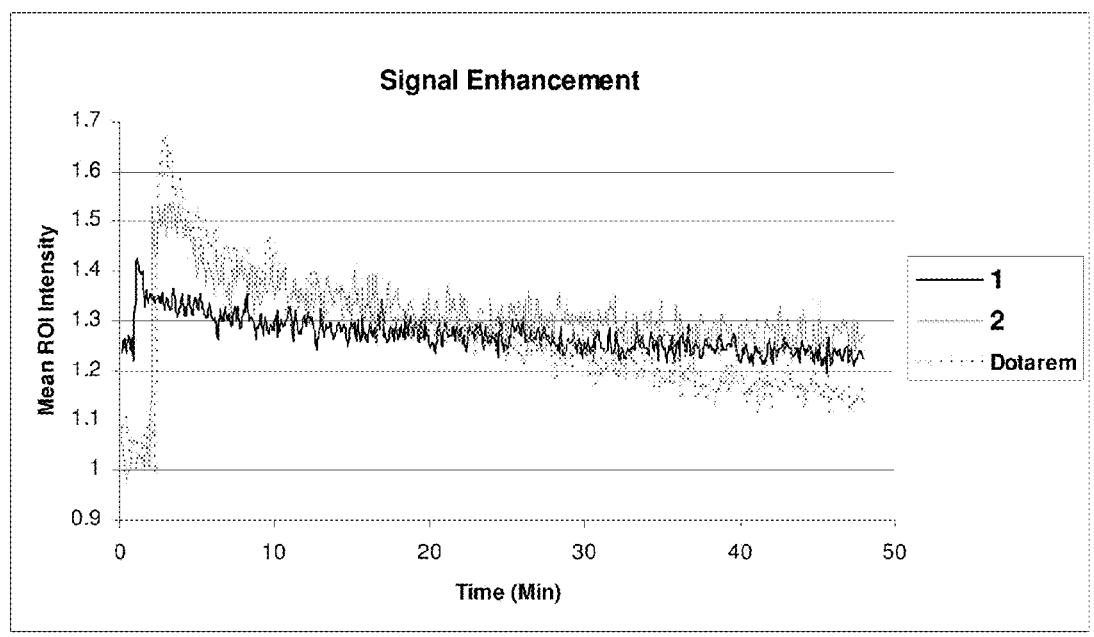

Certain embodiments of the invention are described below, by way of example only, with respect to the accompanying drawings, in which:

FIGS. 1 and 2 show the results of a time course of signal intensity (up to 48 min post injection in brain artery during MRI experiments in Wistar male rat with compounds 1, 2 and Dotarem (dose 0.04 mmol Gd/kg of BW)).

Synthesis of Monomers

Two amino acid monomers derived from glutamic acid, 1 and lysine, 2 were synthesised

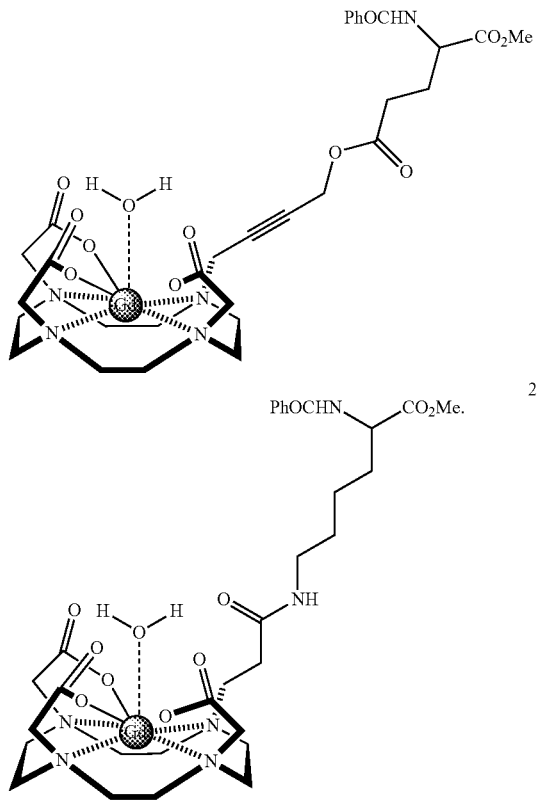

The following experimental procedures were used to synthesis the monomeric amino acid-containing ligands and the subsequent complex formation with GdCl$_3$.

1. Preparation of Compound 1 (Scheme 1)

Intermediate a

A solution of alkyne in dry CH$_3$CN was added to a stirred mixture of starting material and K$_2$CO$_3$ in dry CH$_3$CN. The reaction mixture was stirred at 60° C. for 1 day then filtered and evaporated to dryness to give the crude product which was purified by column chromatography over silica gel (10% MeOH:DCM).

Intermediate b

A suspension of intermediate a in THF was added TBAF and stirred for 18 h. The reaction was diluted with DCM and washed with water (3×), brine then dried over MgSO4, evaporated to dryness to get product.

Intermediate c

A stirred solution of DCC, DMAP in DCM at −5° C. was added a solution of intermediate b in DCM, then solution of glutamic acid derivative in DCM was added dropwise and the reaction mixture was stirred at −5° C. for 18 hours. After that the reaction was filtered and evaporated to dryness. The crude product was purified by column chromatography over silica gel (10% methanol/DCM)

Ligand 1

To a stirred solution of intermediate c in DCM, TFA was added. The reaction mixture was stirred for 20 h. The solvent was removed under reduced pressure and acid chased off by the addition and evaporation of successive portion of DCM 2×10 mL), MeOH (2×10 mL) and diethyl ether (2×10 mL) then lyphilized to give a product.

Compound 1
GdCl$_3$ was added to the solution of 1 equiv of Ligand 1 in 0.5 M ammonium acetate buffer (pH 6). Heating for 2 h is needed to complete the reaction. The pure Compound 1 was obtained after HPLC purified.
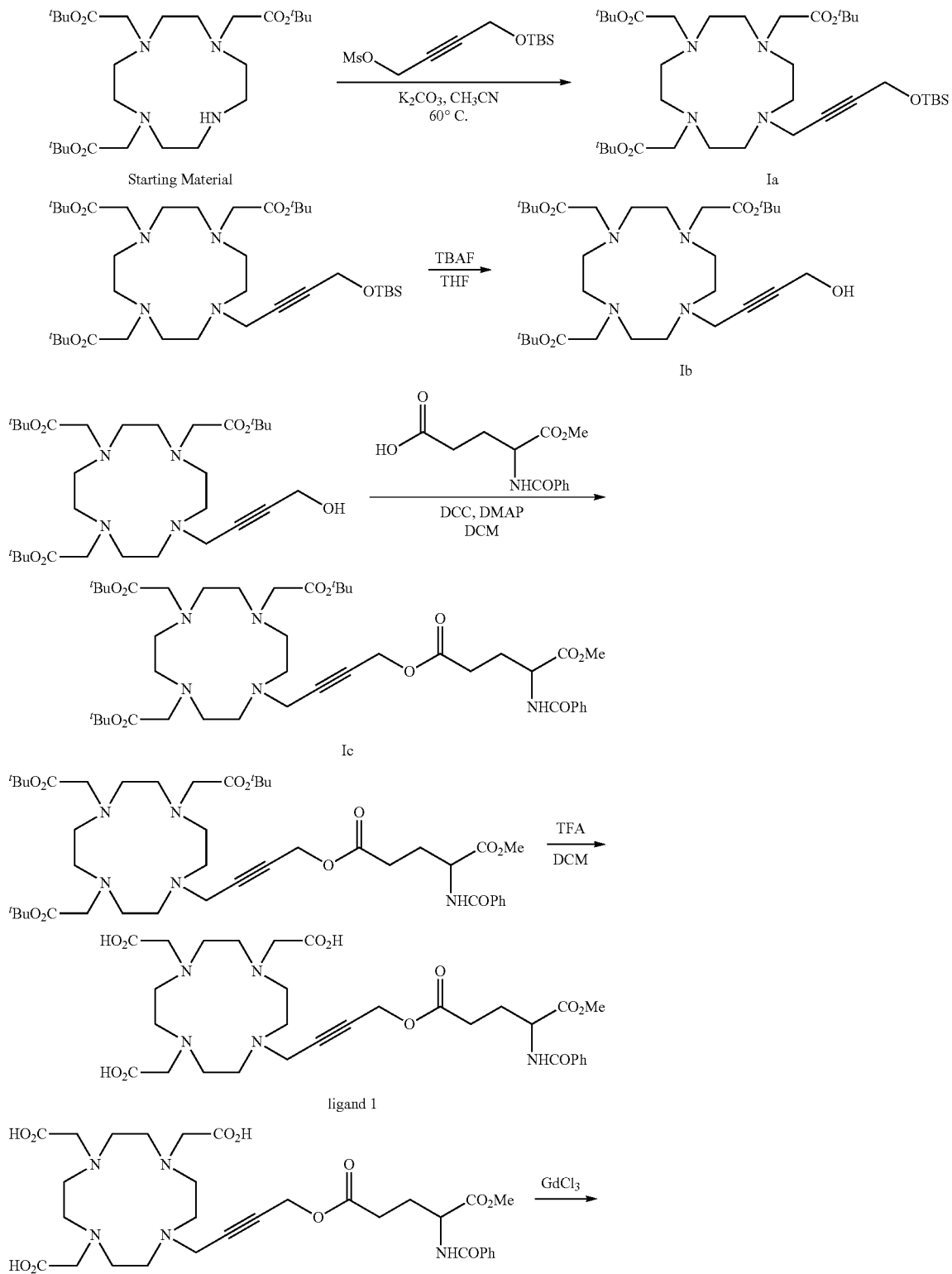
Scheme 1. Preparation of Compound 1

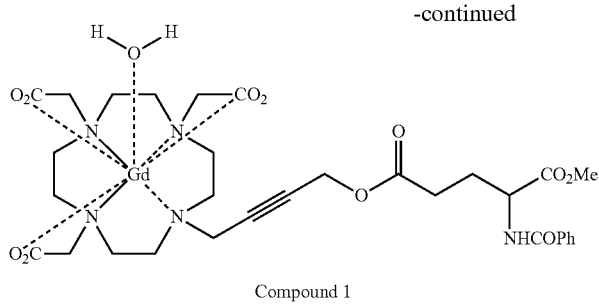

Compound 1

2. Preparation of Compound 1 (Scheme 2)

Intermediate d

To a stirred solution of starting material and methyl acrylate in CH₃CN was added DBU at r.t. After 20 h, the reaction mixture was concentrated and diluted with DCM then washed with aq. NH₄Cl, water and brine, dried over MgSO₄ and evaporated to dryness then purified by column chromatography over silica gel (10% MeOH:DCM)

Intermediate e

A stirred solution of Intermediate d in MeOH/H2O (3:1) was added LiOH and stirred for 16 h. The solvent was evaporated to get product.

Intermediate f

A stirred solution of DCC, HOBt in DCM at 0° C. was added a solution of Intermediate e and DIPEA in DCM, then a solution of lysine derivative in DCM was added dropwise and the reaction mixture was stirred at rt for 2 days. After that the mixture was filtered and evaporated to dryness. The crude product was purified by column chromatography over silica gel (10% MeOH:DCM)

Ligand 2

To a stirred solution of Intermediate f in DCM. TFA was added. The reaction mixture was stirred for 20 h. The solvent was removed under reduced pressure and acid chased off by the addition and evaporation of successive portion of DCM 2×10 mL), MeOH (2×10 mL) and diethyl ether (2×10 mL) then lyphilized to give a product.

Compound 2

GdCl₃ was added to the solution of 1 equiv of Ligand 2 in 0.5 M ammonium acetate buffer (pH 6). Heating for 2 h is needed to complete the reaction. After HPLC purification, Compound 2 was obtained.

Scheme 2. Preparation of Compound 2

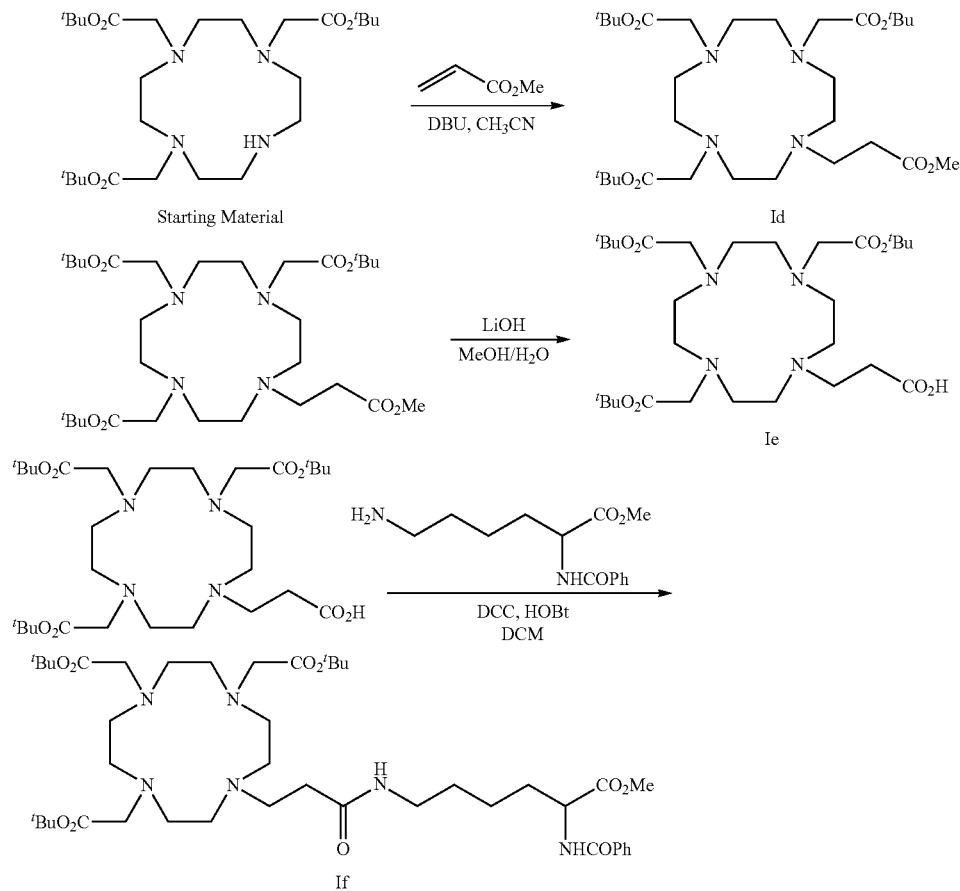

-continued
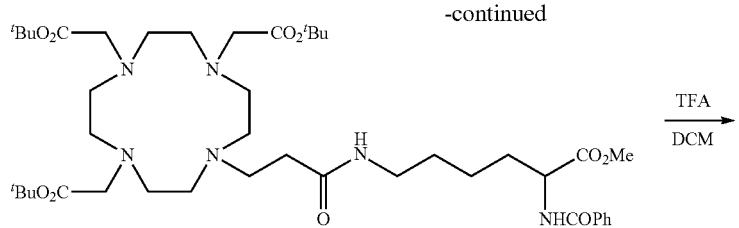
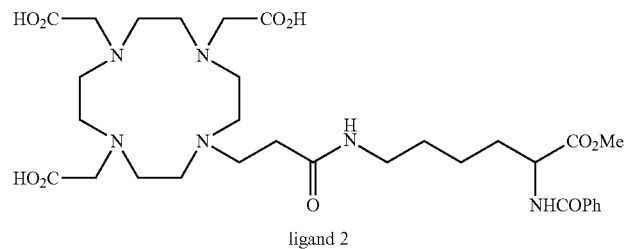
ligand 2
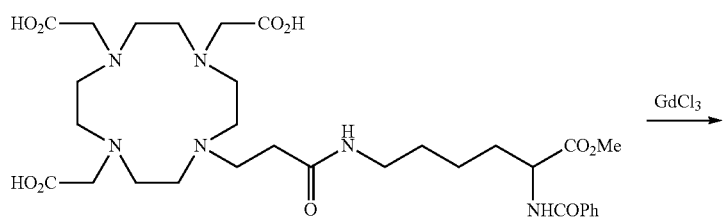
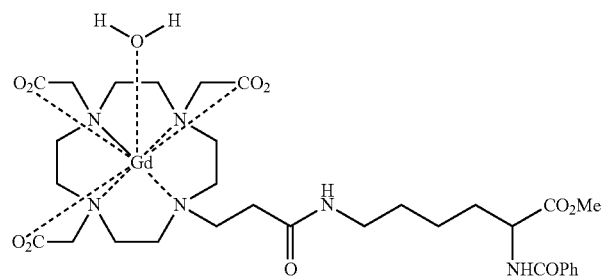
Compound 2
Synthesis of Oligomers
Using the monomeric building blocks discussed above, an oligomeric structure represented schematically below may be synthesised
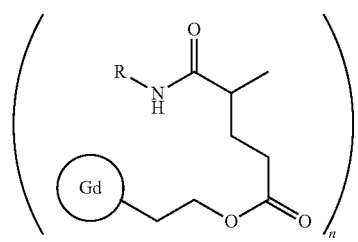
(n = 2-10)

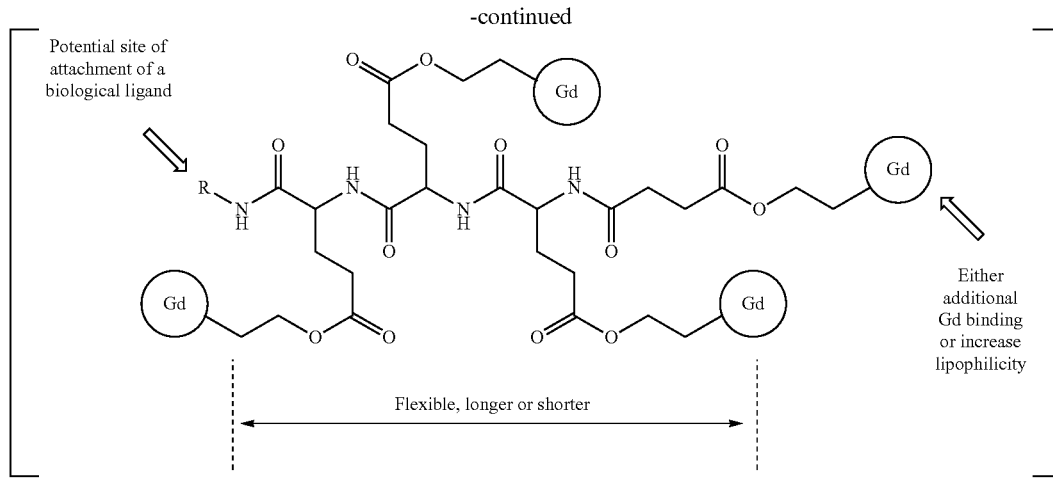

As illustrated in the schematic, control of the number of monomeric units can be used to adjust the properties of the contrast agent. In particular, preferably the number and nature of the monomeric units can be selected so as to adjust the flexibility of the contrast agent and/or adjust its affinity for a particular site in the patient's body. For example, the length of the contrast agent, and in particular the peptide portion, can suitably be adjusted to modify the properties of the contrast agent.

Suitably the amino acid units can be modified or derivatised so as to permit attachment of a biological ligand, suitably a ligand that selectively binds to a binding site in the patient's body. Indeed, in embodiments, the contrast agent includes such a biological ligand.

Suitably the amino acid units can be modified to provide for incorporation of a lipophilic group so as to increase the lipophilicity of the contrast agent. The present invention therefore includes a contrast agent as described herein comprising at least one lipophilic groups.

Typically, the contrast agent comprises between 2 and 10 amino acid units as illustrated above. Suitably each amino acid unit is associated with a Gd chelate, but in embodiments only some (preferably at least 50%) of the amino acid units are coupled to a Gd chelate.

As discussed herein, a particularly preferred Gd chelate is Gd-DOTA and suitably the amino acid unit is coupled to the Gd chelate via a nitrogen in the complexing ligand.

In embodiments, peptide oligomers of specific length containing pre-determined numbers of lysine and glutamate residues with are attached to Gd(III) complexes. Hence, the total amount of Gd is controlled.

A particularly preferred method of attachment of Gd chelate to peptide oligomers is via propionate units incorporated by conjugate addition of a nitrogen atom of the Gd coordinating group to an acrylate ester, followed by attachment to a peptide.

MRI Experiments

Relaxivity measurement and MRI were conducted on a Varian 9.4T MRI system (Palo Alto, Calif., USA). T1 was measured by inversion recovery spin echo in aqueous phantoms with concentrations 0.4, 0.2 0.1, 0.05, 0.025, 0.0125 and 0.00625 mM Gd. In vivo study was conducted on Wistar rats (male, weight 320-340 g) under 2% isoflurane anesthesia. CAs were injected (dosage: 0.04 mmol Gd/kg body weight) through tail vein. T1-weighted images were acquired every 6.4 s for 48 min with T1-weighted gradient echo sequence (TR/TE=50/3 ms, flip-angle=20 degree, resolution=230 mm, thickness=2 mm).

The study of their relaxivity showed the $r_1$ of two monomeric complexes (6.81 and 4.84 mM$^{-1}$s$^{-1}$ for 1 and 2 respectively at 9.4 T, 25° C., in H$_2$O) are both higher than that of the clinical used ones (3.9 and 4.1 mM$^{-1}$s$^{-1}$ for Gd-DOTA and Gd-DTPA respectively at 9.4 T, 25° C., in H$_2$O). Imaging studies of these two complexes demonstrated that contrast enhancement in the brain artery right after i.v. tail vein post injection at 60 seconds (FIG. 1). Time course of signal intensity (up to 15 min post injection) in brain artery during MRI experiments in Wistar male rat showed considerable signal enhancement was found and the contrast agents remained intravascular for at 1 hours.

The invention claimed is:

1. A compound according to the following formula, and pharmaceutically acceptable salts, hydrates, and solvates thereof:

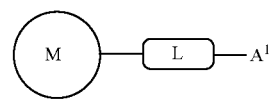

wherein

is a paramagnetic metal chelate comprising a nitrogen-containing macrocycle having at least 3 coordinating nitrogen atoms,

is a linker group, attached directly to a coordinating nitrogen of the macrocycle, selected independently from

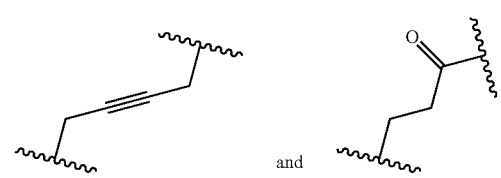

and

A¹ is an amino acid or amino acid derivative selected independently from:

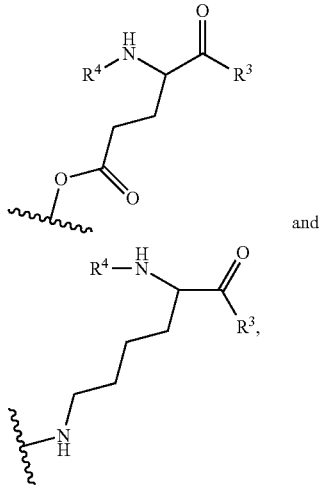

wherein

R3 is selected independently from A² and —OMe, and wherein

A², if present, is selected independently from glutamic acid, a glutamic acid derivative, lysine and a lysine derivative, and R4 is selected independently from A² as defined above and —C(O)-Ph.

2. A compound according to the following formula, and pharmaceutically acceptable salts, hydrates, and solvates thereof:

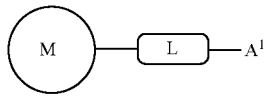

wherein

is a paramagnetic metal chelate comprising a nitrogen-containing macrocycle having at least 3 coordinating nitrogen atoms,

is a linker group, attached directly to a coordinating nitrogen of the macrocycle, selected independently from

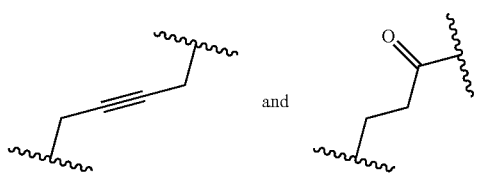

and wherein A¹ is selected independently from:

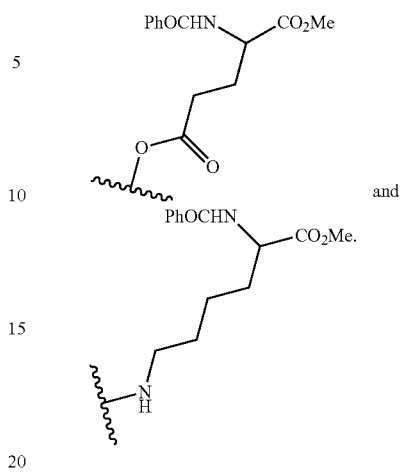

3. A compound according to Formula 1:

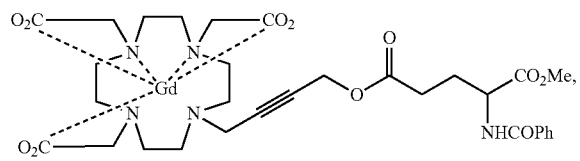

or Formula 2:

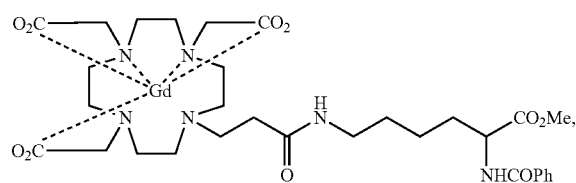

or a pharmaceutically acceptable salt, hydrate, or solvate thereof.

4. A ligand for a contrast agent, wherein the ligand is a compound of the following structure:

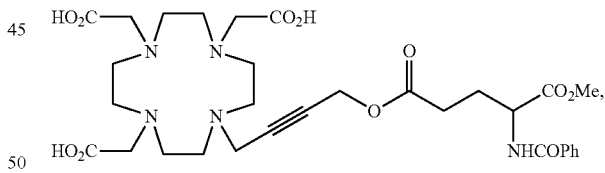

or a compound of the following structure:

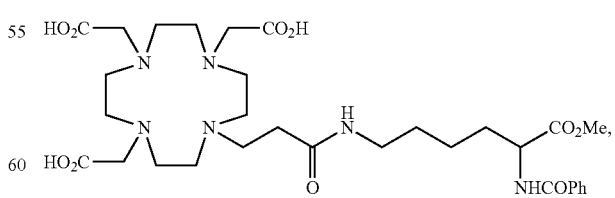

or a pharmaceutically acceptable salt, hydrate, or solvate thereof.

5. A method comprising performing magnetic resonance imaging (MRI) using a contrast agent, wherein the contrast agent is a compound according to claim 1.

6. A method according to claim 5, wherein

is a Gd chelate.

7. A method comprising administering a contrast agent to a patient, wherein the contrast agent is a compound according to claim 1.

8. A method comprising performing magnetic resonance imaging (MRI) using a contrast agent, wherein the contrast agent is a compound according to claim 2.

9. A method comprising performing magnetic resonance imaging (MRI) using a contrast agent, wherein the contrast agent is a compound according to claim 3.

10. A method comprising performing magnetic resonance imaging (MRI) using a contrast agent, wherein the contrast agent is a compound according to claim 4.

11. A method according to claim 8, wherein

is a Gd chelate.

12. A method comprising administering a contrast agent to a patient, wherein the contrast agent is a compound according to claim 2.

13. A method comprising administering a contrast agent to a patient, wherein the contrast agent is a compound according to claim 3.

14. A method comprising administering a contrast agent to a patient, wherein the contrast agent is a compound according to claim 4.

* * * * *